United States Patent
Sadri et al.

(10) Patent No.: US 7,174,787 B2
(45) Date of Patent: Feb. 13, 2007

(54) SYSTEM AND METHOD FOR INSPECTING AN INDUSTRIAL FURNACE OR THE LIKE

(75) Inventors: Afshin Sadri, Woodbridge (CA); Richard deWalle, Brampton (CA)

(73) Assignee: Andec Manufacturing Ltd., Rexdale (CA)

( * ) Notice: Subject to any disclaimer, the term of this patent is extended or adjusted under 35 U.S.C. 154(b) by 0 days.

(21) Appl. No.: 10/388,927

(22) Filed: Mar. 13, 2003

(65) Prior Publication Data

US 2004/0177692 A1 Sep. 16, 2004

(51) Int. Cl.
*G01N 29/06* (2006.01)
(52) U.S. Cl. .............................. 73/597; 73/600; 73/602
(58) Field of Classification Search ................. 73/597, 73/598, 599, 600, 777, 778, 799, 800, 801, 73/803, 818
See application file for complete search history.

(56) References Cited

U.S. PATENT DOCUMENTS

| | | | | |
|---|---|---|---|---|
| 3,982,425 A | * | 9/1976 | McLain ....................... 73/632 |
| 4,165,649 A | * | 8/1979 | Greer, Jr. ..................... 73/644 |
| 4,510,793 A | * | 4/1985 | Ploegaert et al. .............. 73/86 |
| 4,890,496 A | * | 1/1990 | Birring et al. ................. 73/597 |
| 5,092,176 A | * | 3/1992 | Buttram et al. ............... 73/599 |
| 5,975,754 A | * | 11/1999 | Groth et al. .................. 374/45 |
| 6,202,490 B1 | * | 3/2001 | Taniguchi et al. ............. 73/628 |
| 6,598,485 B1 | * | 7/2003 | Lin et al. ...................... 73/803 |
| 2003/0145659 A1 | * | 8/2003 | Momayez et al. ............. 73/800 |

FOREIGN PATENT DOCUMENTS

| JP | 62297710 A | * | 12/1987 |
|---|---|---|---|
| JP | 01074444 A | * | 3/1989 |
| JP | 07268428 A | * | 10/1995 |

OTHER PUBLICATIONS

S. Fujiyosi et. al., "The Developement of Nondestructive Measuring on Refractories for Iron and Steel Making", Oct. 21-26, 1990, The Sixth International Iron and Steel Congress, Nagoya, Japan, pp. 215-222.*

* cited by examiner

*Primary Examiner*—Hezron Williams
*Assistant Examiner*—Rose M. Miller
(74) *Attorney, Agent, or Firm*—Merchant & Gould P.C.

(57) ABSTRACT

A system for inspecting a refractory furnace having an outer shell and an inner refractory brick lining includes a stress wave generator for generating stress waves that propagate through the outer shell and the refractory brick lining. A stress wave sensor senses reflected stress waves returning to the outer shell. A processing unit in communication with the stress wave sensor processes output generated by the stress wave sensor to generate data representing the condition of the refractory brick lining. In this manner, the location and geometry of anomalies within the refractory brick lining can be determined without requiring the refractory furnace to be shut down.

33 Claims, 1 Drawing Sheet

SYSTEM AND METHOD FOR INSPECTING AN INDUSTRIAL FURNACE OR THE LIKE

FIELD OF THE INVENTION

The present invention relates generally to inspection systems and in particular to a system and method for inspecting an industrial furnace or the like.

BACKGROUND OF THE INVENTION

Industrial furnaces are well known in the art. A typical industrial furnace includes a furnace wall comprising an outer shell formed of steel and an inner protective refractory brick lining. Molten materials such as metal or aggressive chemicals are contained in industrial furnaces of this nature and therefore, integrity of the refractory brick linings is of primary concern. The refractory brick lining includes multiple layers of refractory brick with safety refractory brick being disposed between the outer shell and inner refractory brick that is in contact with the molten materials or aggressive chemicals.

Unfortunately, exposure of the refractory brick lining to molten materials or aggressive chemicals tends to deteriorate the refractory brick lining over time resulting in a loss of thickness. As the refractory brick lining deteriorates, molten materials or aggressive chemicals in the industrial furnace may penetrate the inner refractory brick thereby exposing safety refractory brick to the molten materials or aggressive chemicals. This creates discontinuities in the refractory brick lining which over time may result in exposure of the outer shell to molten materials or aggressive chemicals. If this occurs, the outer shell may be compromised placing individuals at risk. As a result, it is necessary to inspect industrial furnaces regularly to determine the condition of the refractory brick linings.

One prior art technique to inspect an industrial furnace makes use of thermal coupling devices in association with numerical modeling techniques to develop a model of the industrial furnace based on known heat transfer characteristics of the refractory material. Unfortunately, this technique suffers disadvantages in that the thermal coupling devices require high maintenance. Also, the model of the industrial furnace is often inaccurate yielding poor results.

Infrared thermographic imaging, ground penetrating radar and laser measurement have also been used to inspect industrial furnaces. Infrared thermographic imaging suffers disadvantages in that this imaging technique only permits imaging of the outer shell and is limited to imaging the first few centimetres of the outer shell. Ground penetrating radar suffers disadvantages in that it cannot be used to image metal surfaces and therefore, it must be used within the industrial furnace. This of course requires inspection to be performed only when the industrial furnace is not in operation. This is also the case for laser measurement which can only be applied to the inside of the furnace, when the furnace is not in operation, so that the laser can measure the loss of thickness from the surface of the inside layer of the refractory brick lining.

None of these above-described techniques permits subsurface deterioration of the overall integrity of the refractory brick layers, the ingress of molten metal between, or into, the individual refractory bricks, or between the layers of refractory brick, to be detected. As a result, limited success has been achieved using these techniques. As will be appreciated, improved techniques to inspect industrial furnaces are desired.

It is therefore an object of the present invention to provide a novel system and method for inspecting an industrial furnace or the like.

SUMMARY OF THE INVENTION

According to one aspect of the present invention there is provided a system for inspecting an industrial furnace wall comprising:

a stress wave generator generating a stress wave that propagates into said industrial furnace wall;

a stress wave sensor sensing stress wave reflections that return to the outer surface of said industrial furnace wall; and a processor coupled to said stress wave sensor and receiving output generated by said stress wave sensor in response to sensed stress wave reflections, said processor processing said output to generate data representing of the condition of said industrial furnace wall.

Preferably, the processor processes the output of the stress wave sensor to determine the location of anomalies within the industrial furnace wall. It is also preferred that the processor processes the output of the stress wave sensor to determine the quantity and geometry of the anomalies within the industrial furnace wall. This enables subsurface deterioration of and ingress of molten metal into the industrial furnace wall to be accurately determined.

Preferably, the stress wave sensor senses compression (P) waves. The processor calculates numerical values of reflected P-waves and compares the numerical values with datum values to determine deviations in the thickness of the industrial furnace wall. It is also preferred that the processor constructs an image of the industrial furnace wall using the calculated numerical values.

According to another aspect of the present invention there is provided a system for inspecting a refractory furnace including an outer shell and an inner refractory brick lining, said system comprising:

a stress wave generator generating stress waves that propagate through said outer shell and refractory brick lining;

a stress wave sensor sensing reflected stress waves returning to said outer shell; and a processing unit in communication with said stress wave sensor, said processor unit processing output generated by said stress wave sensor thereby to generate data representing the condition of said refractory brick lining.

According to yet another aspect of the present invention there is provided a method of inspecting an industrial furnace wall comprising the steps of:

directing a stress wave into said industrial furnace wall;

sensing reflections of said stress wave and generating output in response thereto; and processing the output to generate data representing the condition of said industrial furnace wall.

The present invention provides advantages in that the condition of the industrial furnace wall can be determined accurately from the outside surface of the furnace wall, without requiring the industrial furnace to be shut down. In this manner, subsurface deterioration and the ingress of molten metal between and into refractory bricks and between refractory brick layers can be determined allowing industrial furnaces having compromised refractory brick linings to be detected before a catastrophic event occurs.

BRIEF DESCRIPTION OF THE DRAWINGS

An embodiment of the present invention will now be described more fully with reference to the accompanying drawings in which.

DETAILED DESCRIPTION OF THE PREFERRED EMBODIMENT

Figure 1:
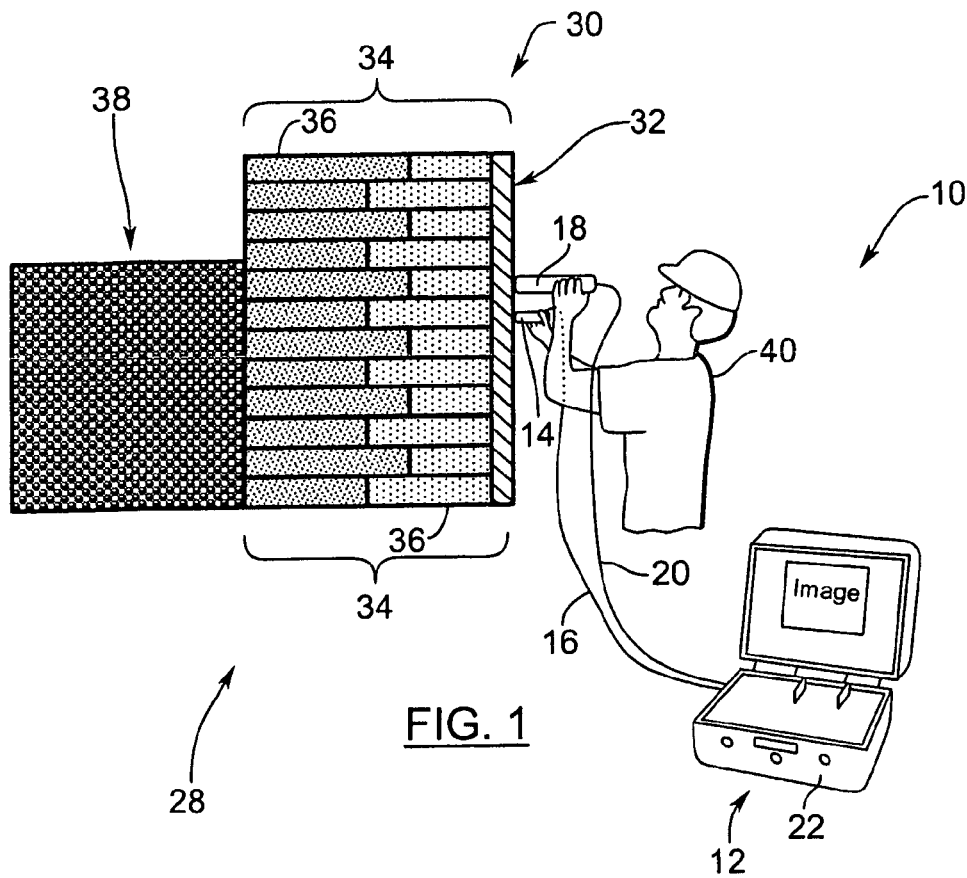
FIG. 1 is a schematic illustration, partly in section of a system for inspecting an industrial furnace.

Turning now to FIG. 1, a system for inspecting an industrial furnace is shown and is generally identified by reference numeral 10. As can be seen, system 10 includes a processing unit 12 coupled to a stress wave generator 14 by a length of cable 16 and coupled to a broadband stress wave sensor 18 by a length of cable 20. The processing unit 12 is disposed in a carrying case 22 that accommodates the stress wave generator 14, the stress wave sensor 18 and the cables 16 and 20 making the system 10 easily transported.

System 10 is particularly suited to inspecting industrial refractory furnaces. FIG. 1 shows an exemplary industrial refractory furnace 28 having a furnace wall 30 that includes an outer shell 32 and a refractory brick lining 34 within the outer shell 32. The outer shell 32 is typically formed of steel. The refractory brick lining 34 includes a number of layers of refractory brick 36 to protect the outer shell 32 from exposure to molten materials or aggressive chemicals 38 contained in the industrial refractory furnace 28.

As mentioned previously, it is desired to inspect industrial refractory furnaces periodically to determine the state of the refractory brick lining 34 so that discontinuities in the refractory brick lining can be detected before a catastrophic event occurs. The system 10 allows the furnace wall 30 to be imaged and discontinuities in the refractory brick lining 34 detected. Further specifics of the operation of the system 10 will now be described with particular reference to FIGS. 1 and 2.

In use, the system 10 is brought by an operator 40 to the location of the industrial refractory furnace 28 to be inspected and the processing unit 12 is placed at a convenient location spaced from the industrial refractory furnace. The processing unit 12 is turned on and the settings are adjusted to accommodate the geometry of the furnace wall 30 to be inspected. The operator 40 then holds the stress wave generator 14 and the stress wave sensor 18 against the outer shell 32 at the location to be inspected. With the stress wave generator 14 and the stress wave sensor 18 properly positioned, the operator 40 activates the stress wave generator 14.

Figure 2:
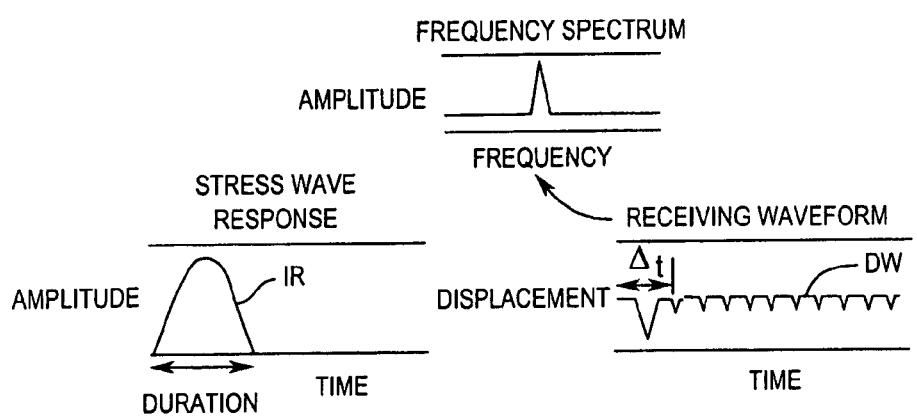
FIG. 2 is a schematic block diagram of the system of FIG. 1.
Figure 2:
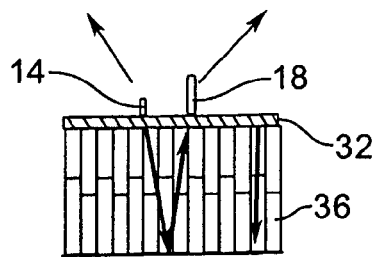

When the stress wave generator 14 is activated, the stress wave generator 14 generates a stress wave that is directed into and propagates through the furnace wall 30. FIG. 2 shows the impulse response IR of the generated stress wave. The stress wave propagating through the furnace wall 30 reflects and returns back to the outer shell 32 from various interfaces within the furnace wall 30. The reflections of the stress wave that return back to the outer shell 32 are sensed by the stress wave sensor 18. The stress wave sensor 18 in turn generates transient electrical impulses in response to sensed stress wave reflections and conveys the electrical impulses to the processing unit 12 via cable 20.

The processing unit 12 in turn captures the transient electrical impulses and stores digitized waveforms DW in memory. Location data representing the physical location of the industrial refractory furnace 28 where the digitized waveforms are acquired is also stored. The location data is entered into the processing unit 12 by the operator 40 either before or after acquisition of the digitized waveforms. The above process is performed at other physical locations of the industrial refractory furnace 28 until the entire industrial refractory furnace has been satisfactorily examined.

Once a sufficient number of digitized waveforms have been acquired, the processing unit 12 performs signal analysis on the digitized waveforms to evaluate and interpret the digitized waveforms. In this manner information concerning the condition of the furnace wall 30 can be developed and output representing the physical condition of the furnace wall 30 generated. Specifics of the signal analysis performed by the processing unit 12 will now be described.

As is known by those of skill in the art, there are three main types of stress waves, namely compression, longitudinal or primary (P) waves; shear, transverse or secondary (S) waves; and Rayleigh or (R) waves.

Compression (P) waves are characterized by longitudinal particle motion. This means that while the P-wave is passing through a medium, particles vibrate about an equilibrium position, in the same direction as the P-wave is travelling. P-waves involve compression and rarefaction, but no rotation of the material while they are passing through an elastic medium.

Shear (S) waves are characterized by transverse particle motion. This means that while the S-wave is passing through a medium, particle displacement is perpendicular to the direction of propagation and motion of the S-wave. S-waves involve shearing and rotation, but no volume changes while they are passing through an elastic medium.

Rayleigh (R) waves are surface waves, which move with marginal attenuation in the direction of wave propagation. In R-waves the particle motion is more or less a combination of longitudinal and transverse vibration. Characteristically, the energy level of R-waves drops rapidly as the R-waves penetrate below the surface.

Stress waves follow the fundamental equation of waves:

$$C = f \times \lambda \quad (1)$$

where C is the wave velocity, f is the wave frequency and $\lambda$ is the wavelength.

The shape of P-waves, S-waves, and R-waves depends on the characteristics of the source that is used to generate the stress waves. There are three idealized types of stress wave wavefronts, namely planer, cylindrical and spherical. In the case of a point source normal to the surface of the medium, the resulting P-waves and S-waves are spherical and the R-wave is circular.

For an infinite elastic solid, the velocity of P-waves is computed by the following equation:

$$C_p = \sqrt{\frac{E(1-\upsilon)}{(1-\upsilon)(1-2\upsilon)\rho}} \quad (2)$$

where E is the Young's modulus of elasticity, $C_p$ is the P-wave velocity, $\rho$ is the density, and $\upsilon$ is the Poisson's ratio.

In rod-shaped structures, where the diameter of the cylinder is much smaller than it's length, d<<1, the P-wave velocity is slower than in an infinite elastic solid and is given by the following equation:

$$C_p = \sqrt{\frac{E}{\rho}} \quad (3)$$

The S-wave velocity $C_s$ is calculated by the following equation:

$$C_s = \sqrt{\frac{E}{2\rho(1+\upsilon)}} \quad (4)$$

R-wave velocity $C_R$ is determined by the following equation:

$$C_R = \frac{0.87 + 1.12\upsilon}{1+\upsilon} C_s \quad (5)$$

Each of the three types of stress waves travels with a different velocity. P-waves have the highest velocity. S-wave velocities are between 0.65 and 0.45 of P-wave velocities, depending on the stiffness of the material. As the material stiffness increases the ratio between the S and P-wave velocities increases. For a Poisson's ratio of 0.2, the S-wave to P-wave velocity ratio is about 0.61. R-wave velocities are the slowest. R-waves have a velocity of roughly 92% of the S-waves (for a Poisson ratio of 0.2) and 56% of P-waves. They are easy to recognize because they have large amplitudes, low frequencies and appear last almost immediately after S-waves. In a simple comparison between P-wave and S-waves of the same frequency, S-waves have smaller wavelengths and amplitudes than P-waves.

Fundamentally, S-waves are subdivided based on their polarization characteristics to radial (SV) and transverse (SH) components. SH-waves have their particle displacements parallel to the boundary surface, and SV-waves have their particle displacements lying in the incident plane. SV-waves are not easily recognizable on a time domain spectrum, since they are coupled with P-waves. On the other hand, SH-waves are self-consistent in the sense that they do not interact with P-waves and SV-waves. This means that SH-waves do not convert into P-waves and/or SV-waves nor do P-waves and/or SV-waves convert into SH-waves.

The encounter of stress waves with an acoustic interface causes reflection, refraction and mode conversion of the waveforms. An acoustic interface is a boundary between two materials with different acoustic impedance. Acoustic impedance Z is defined by the following equation:

$$Z = \rho \times C_p \quad (6)$$

The acoustic impedance of each material and the angle of incidence of the stress wave, control the stresses associated with the wave reflection and refraction. For a P-wave with a normal angle of incidence, the incident and reflected stresses are computed using the following equation:

$$R_p = I_p \times \frac{Z_2 - Z_1}{Z_2 + Z_1} \quad (7)$$

where $I_p$ is the stress associated with incident P-waves, $R_p$ is the stress associated with reflected P-waves, $Z_1$ is the acoustic impedance of the first medium, and $Z_2$ is the acoustic impedance of the second medium.

For example, if a P-wave is reflected from a medium with a lower acoustic impedance $Z_2$ than the acoustic impedance of the initial medium ($Z_2 < Z_1$), the sign (polarity) of the P-wave changes (i.e. refractory brick/air interface). This means that a compression wave changes to a tension wave. However, if the acoustic impedance $Z_2$ is higher than the acoustic impedance $Z_1$ ($Z_2 > Z_1$), the reflected P-wave remains with the same sign as the incident P-wave.

In accordance with the present invention, when the stress wave generator 14 is activated and a stress wave is generated, the stress wave, which propagates into the furnace wall 30, undergoes multiple reflections between the outer shell 32 and the opposite boundary, in this case the molten materials or aggressive chemicals contained within the industrial refractory furnace 28. These reflections are caused by internal anomalies within the refractory brick lining 34 such as subsurface deterioration and the ingress of molten materials between and into refractory bricks and between refractory brick layers. The path length of reflected P-waves is twice the distance from the outer shell 32 to the internal anomaly, 2T. Hence, the travel time t between the successive arrivals of reflected P-waves is a function of P-wave velocity, $C_p$ and is computed using the following equation:

$$t = \frac{2T}{C_p} \quad (8)$$

By monitoring the multiple P-wave reflections, the distance to the anomalies causing the reflections can be determined allowing the nearness of anomalies to the outer shell 32 to be calculated.

Peaks in the amplitude spectrum of the P-wave reflections can be readily converted to the depth of the reflecting interfaces and hence the positions and geometries of the anomalies in the refractory brick lining 34 relative to the outer shell 32 can be determined. A spectral peak plotting technique is used to construct an "image" of the interior of the furnace wall 30.

Calculation verification is performed by acquiring datum information concerning the industrial refractory furnace 28 such as refractory dimensions, cross-sections and the presence of cooling staves. Individual constituents of the industrial refractory furnace are tested separately, outside of the industrial refractory furnace to determine their P-wave velocity. The P-wave velocity and the thickness of the constituent for each layer of the industrial refractory furnace can thus be verified accurately.

As will appreciated, the inspection system 10 allows the integrity of industrial furnaces to be inspected from outside of the industrial furnaces while the industrial furnaces are operating. The inspection system is readily transported allowing it to be used in a variety of environments.

If desired, the processing unit 12 can be stationary and positioned adjacent a refractory furnace to be inspected. In this case, the carrying case for the processing unit is not required.

Although a preferred embodiment of the present invention has been described, those of skill in the art will appreciate that variations and modifications may be made without departing from the spirit and scope thereof as defined by the appended claims.

What is claimed is:

1. A system for inspecting an industrial furnace wall comprising:
   a stress wave generator generating a stress wave that propagates into said industrial furnace wall;
   a stress wave sensor sensing stress wave reflections that return to the outer surface of said industrial furnace wall; and
   a processor coupled to said stress wave sensor and receiving output generated by said stress wave sensor in response to sensed stress wave reflections, said processor processing the output of said stress wave sensor to determine the location, quantity and geometry of anomalies within said industrial furnace wall.

2. A system according to claim 1 wherein said stress wave sensor senses compression (P) waves.

3. A system according to claim 2 wherein said processor calculates values of reflected P-waves and compares the calculated values with datum values to determine deviations in thickness of said industrial furnace wall.

4. A system according to claim 3 wherein said stress wave sensor is a broadband stress wave sensor.

5. A system according to claim 1 wherein said processor is coupled to said stress wave generator.

6. A system according to claim 5 wherein said system is portable.

7. A system according to claim 6 wherein said processor, stress wave generator and stress wave sensor are accommodated in a carrying case.

8. A system according to claim 7 wherein said system is stationary.

9. A system according to claim 3 wherein said processor further constructs an image of said industrial furnace wall using said calculated values.

10. A system for inspecting a refractory furnace including an outer shell and an inner refractory brick lining, said system comprising:
    a stress wave generator generating stress waves that propagate through said outer shell and refractory brick lining;
    a stress wave sensor sensing reflected stress waves returning to said outer shell; and
    a processing unit in communication with said stress wave sensor, said processor unit processing output generated by said stress wave sensor thereby to determine the location and geometry of anomalies within said refractory brick lining.

11. A system according to claim 10 wherein said processing unit further generates an image of said refractory brick lining.

12. A system according to claim 10 wherein said anomalies include subsurface deterioration of said refractory brick lining and/or the ingress of molten materials into said refractory brick lining.

13. A system according to claim 12 wherein said stress wave sensor senses compression (P) waves.

14. A system according to claim 13 wherein said processor calculates values of reflected P-waves and compares the calculated values with datum values to determine deviations in thickness of said industrial furnace wall.

15. A system according to claim 14 wherein said processor further constructs an image of said industrial furnace wall using said calculated values.

16. A method of inspecting an industrial furnace wall comprising the steps of:
    directing a stress wave into said industrial furnace wall;
    sensing reflections of said stress wave and generating output in response thereto; and
    processing the output to generate data representing the location and geometry of anomalies within said industrial furnace wall.

17. The method of claim 16 wherein said directing and sensing steps are performed at multiple locations over said industrial furnace wall.

18. The method of claim 17 wherein during said sensing, reflected compression (P) waves are sensed.

19. The method of claim 18 wherein during said processing numerical values of reflected P-waves are calculated and compared with datum values to determine deviations in thickness of said industrial furnace wall.

20. The method of claim 17 wherein said anomalies include subsurface deterioration of said industrial furnace wall and/or the ingress of molten materials into said industrial furnace wall.

21. A system for inspecting an industrial furnace wall comprising:
    a stress wave generator generating a stress wave that propagates into said industrial furnace wall;
    a stress wave sensor sensing stress wave reflections that return to the outer surface of said industrial furnace wall; and
    a processor coupled to said stress wave sensor and receiving output generated by said stress wave sensor in response to sensed stress wave reflections, said processor processing said output and generating data representing the quantity and geometry of anomalies within said industrial furnace wall.

22. A system according to claim 21 wherein said stress wave sensor senses compression (P) waves.

23. A system according to claim 22 wherein said processor calculates values of reflected P-waves and compares the calculated values with datum values to determine deviations in thickness of said industrial furnace wall.

24. A system according to claim 23 wherein said stress wave sensor is a broadband stress wave sensor.

25. A system according to claim 23 wherein said processor further constructs an image of said industrial furnace wall using said calculated values.

26. A system for inspecting a refractory furnace including an outer shell and an inner refractory brick lining, said system comprising:
    a stress wave generator generating stress waves that propagate through said outer shell and refractory brick lining;
    a stress wave sensor sensing reflected stress waves returning to said outer shell; and
    a processing unit in communication with said stress wave sensor, said processor unit processing output generated by said stress wave sensor thereby to generate data representing the quantity and geometry of anomalies within said refractory brick lining.

27. A system according to claim 26 wherein said processing unit further generates an image of said refractory brick lining.

28. A system according to claim 27 wherein said anomalies include subsurface deterioration of said refractory brick lining and/or the ingress of molten materials into said refractory brick lining.

29. A system according to claim 28 wherein said stress wave sensor senses compression (P) waves.

30. A system according to claim 29 wherein said processor calculates values of reflected P-waves and compares the calculated values with datum values to determine deviations in thickness of said industrial furnace wall.

31. A method of inspecting an industrial furnace wall comprising the steps of:
   directing a stress wave into said industrial furnace wall;
   sensing reflections of said stress wave and generating output in response thereto; and
   processing the output to generate data representing the location, quantity and geometry of anomalies within said industrial furnace wall.

32. The method of claim 31 wherein said directing and sensing steps are performed at multiple locations over said industrial furnace wall.

33. The method of claim 32 wherein during said processing a spectral plot image of said industrial furnace wall is constructed.

* * * * *